United States Patent
Wang et al.

[11] Patent Number: 5,922,617
[45] Date of Patent: Jul. 13, 1999

[54] RAPID SCREENING ASSAY METHODS AND DEVICES

[75] Inventors: Mark S. Wang, Redwood City; Limin Li, Palo Alto, both of Calif.

[73] Assignee: Functional Genetics, Inc., Palo Alto, Calif.

[21] Appl. No.: 08/968,659

[22] Filed: Nov. 12, 1997

[51] Int. Cl.⁶ .................................................. G01N 33/533
[52] U.S. Cl. ........................ 436/518; 422/50; 422/55; 422/64; 422/67; 422/82.05; 422/82.11; 422/99; 435/6; 435/7.1; 435/7.5; 436/523; 436/172; 436/805; 436/809; 204/406
[58] Field of Search .................................. 422/50, 55, 64, 422/67, 82.05, 82.11, 99; 435/6, 7.1, 7.5; 436/518, 523, 172, 805, 809; 204/406

[56] References Cited

U.S. PATENT DOCUMENTS

| | | |
|---|---|---|
| 4,737,464 | 4/1988 | McConnel et al. . |
| 5,585,069 | 12/1996 | Zanzucchi et al. . |
| 5,585,639 | 12/1996 | Dorsel et al. . |
| 5,661,028 | 8/1997 | Foote . |
| 5,795,714 | 8/1998 | Cantor et al. . |
| 5,807,522 | 9/1998 | Brown et al. . |
| 5,837,859 | 11/1998 | Teoule et al. . |
| 5,846,708 | 12/1998 | Hollis et al. . |

OTHER PUBLICATIONS

Schlichting et al, Jpn. J. of App. Phys., 36(1B), 1997 pp. 587–588.

Dvornikov et al. Trans. Comp. Pack. & Manuf. Tech. A vol. 20(2), 1997.

Primary Examiner—James C. Housel
Assistant Examiner—Bao-Thuy L. Nguyen
Attorney, Agent, or Firm—Bertram I. Rowland; Rae-Venter Law Group P.C.

[57] ABSTRACT

Methods and apparatus are employed for determining interactions between different components, of the same or different type of composition. The apparatus provides for arrays of samples in tracks, where light emitting labels are excited and emitted light detected. Headers are provided for defining sites, so that particular interactions can be rapidly detected. Particularly, disks having circular tracks with headers defining sites on the tracks, so that positive signals can be interpreted in relation to the information provided by the header. Various modifications can be made, such as preprepared segments which may then be attached to the disk for assaying.

8 Claims, 9 Drawing Sheets

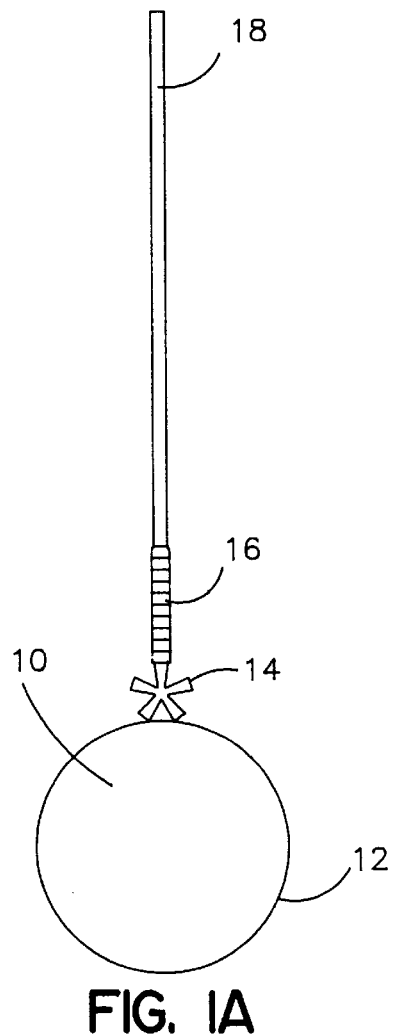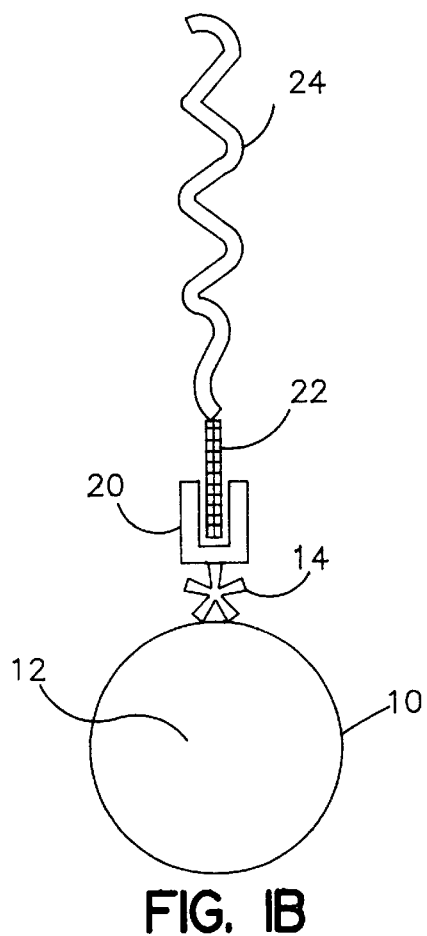

OUTSIDE FOCUS

IN FOCUS

INSIDE FOCUS

RAPID SCREENING ASSAY METHODS AND DEVICES

Concomitant with and an essential adjunct of the biotechnology revolution has been the enormous expansion of materials, information and modes of information handling. Developments, such as combinatorial chemistry, the polymerase chain reaction, recombinant differential analysis, to name only a few, have opened avenues to identifying substances, which may serve as drugs, as targets for drugs, as components in the etiology of diseases, and the like. Because of the plethora of entities being capable of being manipulated and investigated, numerous techniques are evolving to allow for the rapid investigation of a large number of entities.

Among the techniques are arrays of bound components using semiconductor techniques for placing specific substances at microscopic sites by masking and binding substances to the exposed portions of the surface. See, for example, U.S. Pat. No. 5,578,832. Other techniques include the inventions of U.S. Pat. Nos. 5,663,242 and 5,604,097 and the references cited therein.

Desirably, one wishes to have a rapid accurate way for investigating interactions between different compounds or types of compounds. For example, one may wish to investigate ligand- receptor binding, protein-protein interactions, nucleic acid-nucleic acid interactions, carbohydrate-protein interactions, nucleic acid-protein interactions, etc., or more complex interactions involving three or more components. In some instances, one may wish to have a single source, which may be a single or multi-component source, interact with a multi-component screen, or vice-versa. The potential permutations and combinations are extremely large. In addition, one may wish to use the same screen repetitively or for a single analysis. One may wish to probe a portion of the screening array with one or more different entities, a single time or a plurality of times, one may wish to probe a portion or all of the array with consecutive samples or reagents, and the like. Since the variety of protocols is large, it is desirable to have a single system which allows for most or all of the protocols one may wish to use.

In any array, there must be a way to identify the component at any given site. The less area required by a specific bound component, the more information which may be derived from a specific area. Therefor, the desirable close proximity of different bound components requires a system that can accurately detect and differentiate different components which are in physical proximity. The system must allow for the determination of the nature of the component present at a particular site and the result of adding other substances to such site in order to determine the interaction with the bound component. In developing a system, one must consider how the bound component will be organized or registered on a substrate, how it will be capable of being monitored as to its particular position(s), how to ensure that each component is segregated so as to be independently detectable, how to contact a sample and/or reagent with the bound component and how to detect interactions between the bound component and the sample and/or reagent. Each of these stages in the process requires a high degree of accuracy and efficiency to ensure that the signal is not obscured by noise and that one has an efficient and rapid method for screening large numbers of samples and reagents.

SUMMARY OF THE INVENTION

Methods and devices are provided for the efficient and rapid screening of large numbers of components, where the variety may be in either or both a bound first component or a soluble second component, where one is interested in determining the occurrence of an interaction between the first and second components. The devices are: (1) a solid support upon which the bound component(s) have been placed in a predetermined registry in conjunction with address encoders; and (2) a reader for detecting the interaction between the first and second components. The methods involve: (1) preparing the solid support for attachment of the first components; (2) combining the first and second components to effect any interaction between the two components; and (3) determining the presence of an interaction between the first and second components and particular sites.

BRIEF DESCRIPTION OF THE DRAWINGS

FIGS. 1A and 1B are cartoons of a nucleic acid or protein, respectively, attached to a magnetic bead;

FIG. 10 is a diagram of the electronic and computer control system.

DESCRIPTION OF THE SPECIFIC EMBODIMENTS

Figure 2E:
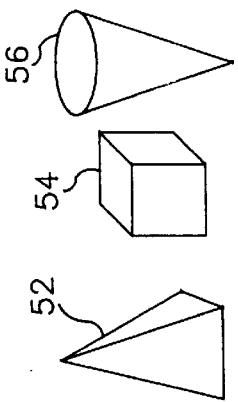
FIG. 2E is a depiction of perspective views of differently shaped particles.

In accordance with the subject invention methods and devices are provided for rapidly screening a large number of events. The invention comprises as devices (1) a microarray of bound components; and (2) a reader for determining the occurrence of events of interest on the microarray. The methods comprise: (1) the preparation of the microarray; (2) combining the microarray with one or more liquid media; and (3) determining the occurrence of events on the microarray, where the events involve the interaction of the bound components in the microarray with added sample, reagents, etc.

The microarray will normally involve a plurality of different components. In theory there need be only one component, but for the most part there will usually be at least 10, more usually at least 20, frequently at least 50, desirably 100 or more, and even 1,000 or more, but usually not more than about $10^5$, more usually not more than about 50,000. While theoretically the number of different components could exceed $10^5$, due to the ability to specifically have a small amount or volume at a specified finite site, for the most part there is no need to exceed 100,000 and such large numbers of different components does add some complexity to the preparation of the microarray. While the number of components will usually not exceed $10^5$, the number of individual addressable sites may be substantially larger, depending on the nature of the bound component, the source of the signal, the nature of the signal which is detected, the sensitivity with which the signal may be detected, the nature of the bound array, such as the size of the microarray, the manner in which the microarray is produced, and the like.

The bound component will normally be an organic entity, usually a single molecule, generally of at least about 125 daltons and not more than about $5\times10^6$ daltons. However, assemblages of molecules may also be used as in the case of organelles, e.g. nuclei, mitochondria, plastids, liposomes, etc., or cells, both prokaryotic and eukaryotic. The bound component may be directly bound to a solid substrate or indirectly bound, using one or more intermediates, which intermediates may serve as bridges between the bound component and the solid substrate. The intermediates may involve chemical entities or physical entities, where the chemical entities may involve covalent or non-covalent bonding, direct covalent bonding to the solid substrate or binding through a chemical bridge. Alternatively, a physical bridge may be employed, where a particle is employed which binds to the solid substrate. Non-covalent binding may involve ligand and receptor binding, nucleic acid-nucleic acid binding, magnetic binding, host-guest binding, and the like. In addition, to enhance the binding between the two entities, one may provide for the formation of covalent bonding, as a result of thermal or photoactivation, using a chemically reactive moiety which will bond after the two entities are complexed, using a chemically reactive moiety which is chemically activated, and the like. See, for example, U.S. Pat. No. 5,565,324 and references cited herein, which are hereby specifically incorporated herein.

For general application, where a molecule is to be covalently bonded to the solid substrate surface, the surface may be activated using a variety of functionalities for reaction, depending on the nature of the bound component and the nature of the surface of the solid substrate. Thus the surface of the solid substrate, if required, may be modified by the introduction of functionalities which may then react with the bound component.

For ligands and receptors, one may employ natural combinations or specific binding pairs, such as antibodies and ligands, biotin and avidin or streptavidin, substrates and enzymes, carbohydrates and lectins, naturally occuring receptors, such as cellular or subcellular receptors and their natural or synthetic ligands, and the like. Alternatively, one may prepare antibodies, particularly monoclonal antibodies, to particular haptens or antigens, and use the combination as a specific binding pair. For example, digoxin and antidigoxin are commercially available.

For nucleic acid bound components, one may use a variety of approaches to bind the nucleic acid to the solid substrate. By using chemically reactive solid substrates, one may provide for a chemically reactive group to be present on the nucleic acid, which will react with the chemically active solid substrate surface. For example, by using silicate esters, halides or other reactive silicon species on the surface, the nucleic acid may be modified to react with the silicon moiety. One may form silicon esters for covalent bonding of the nucleic acid to the surface. Instead of silicon functionalities, one may use organic addition polymers, e.g. styrene, acrylates and methacrylates, vinyl ethers and esters, and the like, where functionalities are present which can react with a functionality present on the nucleic acid. For example, amino groups, activated halides, carboxyl groups, mercaptan groups, epoxides, and the like, may be provided in accordance with conventional ways. The linkages may be amides, amidines, amines, esters, ethers, thioethers, dithioethers, and the like. Methods for forming these covalent linkages may be found in U.S. Pat. No. 5,565,324 and references cited therein.

One may prepare nucleic acids with ligands for binding and sequence tags by primer extension, where the primer may have the ligand and/or the sequence tag, or modified NTPs may be employed, where the modified dNTPs have the ligand and/or sequence tag. Techniques include primer extension, using a ligand and sequence tag labeled oligo primer with ssDNA, DNA polymerase, and dNTPs, to provde after denaturation the single stranded DNA with the ligand and the sequence tag; one may use dsDNA with an overhang as part of a restriction site, fill in with the Klenow fragment and dNTPs, to provide after denaturation the ssDNA with the ligand and sequence tag; or use PCR with a primer having the ligand and sequence tag, to provide after denaturation the ssDNA with the ligand and sequence tag; by direct incorporation of the ligand and sequence tag during oligo synthesis; or by employing an oligo labeled with a sequence tag and extending with terminal transferase and a ligand labeled modified dNTP, e.g. biotin-16-ddUTP. The sequence tag comprising a unique oligonucleotide, usually of from about 8 to 36 nucleotides, if unique, can be used to identify the ligand to which it is attached or, otherwise, to allow for determining the number of ligands present. By using a complementary fluorescent oligonuclotide for hybridization to the sequence tag, the fluorescence can be determined as a measure of the number of ligands present. For identification, the sequence tag can be amplified and then assayed using an appropriate oligonucleotide array. The presence of dsDNA may be determined using a fluorescent dsDNA binding protein.

For RNA, one may use in vitro transcription, using a bacteriophage promoter, e.g. T7, T3 or Sp6, and a sequence tag encoded by the DNA, and transcribe using T7, T3 or Sp6 polymerase, respectively, in the presence of NTPs including a labeled NTP, e.g. biotin-16-UTP, where the resulting RNA will have the oligonucleotide sequence tag at a predetermined site and the binding ligand relatively randomly distributed in the chain.

Less desirable, but useful are single strand and double strand binding proteins, which do not require that there be a binding ligand attached to the nucleic acid. These proteins may be bound to the solid substrate surface by chemical means or by adhesion. In either event, the binding proteins will be available for binding the nucleic acid and retaining the nucleic acid at the surface.

One may prepare a solid substrate with the same or different oligonucleotides on the surface of the solid substrate to serve as capturing oligonucleotides. One may then prepare nucleic acids having the desired sequence with a terminal sequence complementary to the capturing sequence on the solid substrate surface. Various protocols may be used, depending upon whether the sequences on the solid surface are different and define different sites for different sequences or are the same and the different sequences at different sites result from placement of the bound component at a specific site. By providing either the capturing oligonucleotide or the complementary sequence with a reactive species which may be activated, after providing for double strand formation at the desired stringency to minimize mismatches, the reactive species may be activated to form a covalent bond. Photoactivatable compounds include the psoralens, isopsoralens, etc. While not as convenient, both the capturing oligonucleotide and the complementary sequence may be modifed to react with each other, as in the case of Diels-Alder additions, reductive amination, etc.

For proteins, one may use fusion proteins, which can be prepared by fusing an oligonucleotide encoding an epitopic tag with the polypeptide or protein, the poly(amino acid) bound component. Alternatively, one may use a fusion protein comprising a fluorescent dye, e.g., green fluorescent protein, or enzymzyme or a portion of an enzyme, such as β-galactosidase, where the α-fragment is necessary for activity of the larger fragment. By adding the larger fragment to the fusion protein and substrate, where the substrate is a precursor to a fluorescent dye, a sensitive amplifiable detection system is provided. The fusion construct may be introduced into a plasmid or virus and the fusion protein expressed in vitro or the plasmid introduced into an appropriate expression host and the protein expressed in vivo. If one wishes, one may use a eukaryotic host and a signal sequence, so as to express and secrete the fusion protein. The protein may then be isolated and purified. Alternatively, one may bond a ligand, such as biotin or an haptenic molecule to the protein to provide for binding to a receptor. Where a receptor naturally exists, which binds to a site which does not interfere with the role of the protein, such receptor may find use. By having receptors bound to the surface of the solid substrate, the receptor will bind the poly(amino acid) bound component.

The various species may be placed at specific sites using ink jet printing as described in U.S. Pat. No. 4,877,745, photolithography (See, U.S. Pat. No. 5,593,839), silk printing, offset printing, stamping, mechanical application with micropipets using an x-y stage or other rastering technique, or other method which provides for the desired degree of accuracy and spatial separation in placing the bound component. One may provide for activation at a particular site(s), so that reaction can only occur at the activated site; one may apply the bound component at a designated site(s), so that binding only occurs at that site; one may remove a protective coating at a particular site(s), so that binding can only occur at that site(s); one may apply a mask, so that the bound component can only interact with the solid surface at sites where the mask has been removed; and the like.

It many instances it will be desirable to draw a plurality of sample simultaneously, for example, from a 96 well plate. For this purpose, an array of tips can be mechanically assembled, where the tips may provide for a vacuum, be magnetic or other means for gripping and transferring a particle. The device would simultaneously introduce the tips into the plurality of wells and each tip would withdraw a particle. The device would then be reoriented, if necessary, to mirror the orientation of the tracks of the disk, and moved into juxtaposition with disk. The particles would then be released into the tracks of the disk, where orientation and release could be monitored with a laser beam or videocamera.

In a different approach, one may use magnetic beads with a magnetic or magnetizable solid substrate. The bound component may be bound to the magnetic bead by any convenient means, using any of the methods described for use with the solid support. Of particular interest is the use of a ligand and a receptor, particularly biotin and (strept)avidin. By coating the magnetic bead with streptavidin, by itself or in conjunction with another protein to control the binding density of the bound component, the bead can then be used to bind biotin present on the bound component to strongly bind the bound component to the bead. In this way, one can create a library of beads, each composition having beads with a known bound component. The beads may then be bound at specific sites to the solid substrate and held at the site by magnetic forces. One may have a solid substrate which is magnetized, so that the beads will bind wherever they are placed or one may have a solid substrate which may be individually magnetized at different sites, e.g. electromagnetically, so that the beads will bind at the site that is magnetized. The different beads may be added consecutively with different positions being magnetized. By having grooves in the solid substrate, once the bead has settled into the groove, it will be retained there by physical forces. After completion of the addition of the beads, one may magnetize the entire solid substrate to ensure that the beads remain at their sites during the assay.

While rounded beads are readily available and, therefore, most convenient, the particles may have any shape, including but not limited to conical, cylindrical, cubic, platter-form, etc. The magnetic particles carrying the bound component can be isolated by magnetized needles or microvactium devices and precisely arrayed on a solid surface in desired patterns. The positions of the beads may be fixed by a modified magnetic surface with presized holes or pits. While the solid substrate can be any two-dimensional shape, the preferred shape is a disk, similar to a commercial compact disk (CD). High density arrays can be accomplished by one or multiple linear array units with a rotating disk, each linear array unit comprises a set of beads and when positioned on the solid substrate places the set of beads on the disk surface. Micromachined array section units can be generated and the entire disk array can then be accomplished by rotating the disk section by section and applying the beads to each section in accordance with a particular pattern of application. In accordance with the same principle, the whole disk is arrayed using different sizes of circular array sections, which have been individually prepared and fit onto a support in a predetermined pattern. Another strategy is to array many sections or units of a predetermined shape, e.g. quadrilateral, including square, or other convenient shape, according to the number of molecules to be arrayed. One or multiple sections or units are then assembled onto the disk at the desired numbers of bound components.

The average size of the magnetic beads will usually be greater than $1\mu$ and less than about $100\mu$, generally being in the range of about 3 to $50\mu$, preferably from about 3 to $30\mu$. Of course, only a portion of the bead will be exposed, so that the surface area which is available for the screening will be substantially less than the total surface area of the beads. By using small beads, not greater than about $10\mu$, the bound component can be arrayed at high density. More than one $10^6$ beads can be arrayed on less than a 2×2 cm solid surface, although arrays of lower density may also be employed. For example, the entire human expressed sequence tags (ESTs, fewer than $10^6$) can be arrayed on a single 2×2 cm solid surface. This allows for a microarray of genomic DNA fragments representing the entire human genome and genomes of other organisms. The ability to array such large numbers of molecules enables multiple controls and/or multiple genetic materials to be incorporated in a single array. Using the various techniques of this invention, particularly the magnetic beads, provides great flexibility, where the bound components can be arrayed in any numbers or sizes, and with the beads, the arrays are reversible and can be retrieved for further processing.

Regardless of the manner in which the bound component is bound to the solid substrate, for the most part, each bound component will occupy from about 1 to 200μ of the surface of the solid substrate. The number of molecules per site (where a site intends an independent observation or measurement) will generally be in the range of about 20 to $10^6$, more usually in the range of about $10^3$ to $10^6$. Usually, at least 20%, more usually at least about 40% of the total number of molecules present will be available for detection.

One may encode invidual particles, so that if a particle provides a positive signal, one may isolate the particle and decode the particle. For example, one may use a binary code of an homologous aliphatic sequence, with a few different aromatic halides which are releasable from the particle, e.g., photolabile. See, U.S. Pat. No. 5,565,324. After isolating the particle, the coding molecules may be photolysed and read in a capillary electrophoresis-electron capture device. By using a binary code, with a relatively few molecules, a large number of particles, generally greater than about 25,000 may be individually encoded and detected accurately.

For detection, light detectable means are preferred, although other methods of detection may be employed, such as radioactivity, atomic spectrum, and the like. For light detectable means, one may use fluorescence, phosphoresence, absorption, chemiluminescence, or the like. The most convenient will be fluorescence, which may take many forms. One may use individual fluorescers or pairs of fluorescers, particularly where one wishes to have a plurality of emission wavelengths with large Stokes shifts, e.g. ≧20 nm. Illustrative fluorescers which have found use include fluorescein, rhodamine, Texas red, cyanine dyes, phycoerythrins, thiazole orange and blue, etc. When using pairs of dyes, one may have one dye on one molecule and the other dye on another molecule which binds to the first molecule. For example, one may have one dye on the first or bound component and the other dye on the second or complexing component. The important factor is that the two dyes when the two components are bound are close enough for efficient energy transfer.

The arrays may be used in a variety of ways for determining a wide variety of interactions. A straight forward determination is the presence of complementary nucleic acids in a sample. This can be used for forensic medicine, detection of pathogens, both prokaryotic and eukaryotic, identification of specific genes and mutations, such as genetic defects, antibiotic resistance genes, etc., identification of species, sexing, genetic relationships, detection of transcription and cell type, identification of cancerous or other aberrant cells, identification of restriction fragment length polymorphisms, etc.

Besides having nucleic acid interactions, one may have protein interactions, which may be with nucleic acids, other proteins, lipids or carbohydrates. Interactions of interest include binding of transcription factors to nucleic acids or other transcription factors, receptor-ligand binding, lectin-carbohydrate binding, adhesion molecule binding, immunoglobulin binding, virus-surface membrane protein binding, etc.

In addition, the subject technique can be used with techniques employed with combinatorial chemistry, where individual beads are coded for their synthetic pathway and have numerous copies of a single compound bound to the bead. The beads may be magnetized or labeled so as to become bound to the solid substrate. By using one or more labeled proteins of interest, one may detect which of the compounds of the library bind the proteins of interest. To enhance signal, one may use a ligand bound to the protein and then couple with a fluorescent bead-receptor conjugate in a one- or two-step process. Other situations where one has a large number of candidates associated with beads may also be used including various forms of combinatorial chemistry using particles. In addition, one may use transfers from various separation methods, such as microgel electrophoresis. Alternatively, one may place microsamples of effluents from liquid chromatographs, or other microsized separation technique.

The solid substrate may take many forms, limited to the ability to segregate components, address sites of the solid substrate to determine the occurrence of events, provide for stability of the distribution of the bound component and the interaction with the mobile component, ease of production, and the like. While other peripheral forms or surface shapes may find use, such as rectangular, irregular, regular, or the like, a circular form capable of rotation around a central axis will be the most convenient. The solid substrate may have a central orifice for mounting on a post and be positioned on a support for circular movement or sit on a support which moves circularly, moving the solid substrate with it, or be mounted on a spindle which rotates, without a support for the solid substrate. The solid substrate may have a plurality of circular grooves, which may have a smooth wall surface, generally U-shaped, although other shapes may find use, such as generally V-shaped, corrigated walls, flat-bottomed, etc., where the walls of the groove may be normal to the plane of the solid substrate surface or at an acute angle to the surface, usually not less than 45° from the surface. The depths of the grooves will usually be at least about 2μ, more usually at least about 3μ, and generally not more than about 500μ, more usually not more than about 250μ, with the width of the groove coming within the same limitations. Generally, the cross-section of the groove will be at least about 5μ, usually in the range of about 5 to 5000μ, more usually in the range of about 25 to 1000μ. Grooves will usually be separated by walls of at least about 1μ, more usually at least about 2μ, preferably at least about 5μ. The wall can be any thickness greater than the minimum, depending on the size of the solid substrate, the number of grooves desired, the separation required for efficient detection and the ease of fabrication. Desirably, the separation between two sites to be measured will be less than about 100μ.

The bottom surface can be varied widely in relation to the manner in which the protocol is carried out and the information to be provided. For example, where particles are used, the bottom of the groove may have a complementary shape to the particle, providing for round, cylindrical, conical, or other convenient complementary or accommodating shape, e.g., a rectangular pit capable of accommodating a round or cylindrical particle. Thus, the particles can be spaced apart in the groove in relation to the spacing of the pits in the groove.

The particular manner in which the bound component is bound will affect the packing density of the bound component, so that different approaches to binding may be employed depending upon the localized concentration of the bound component which is desired. One can create arrays, where a single bound component is one or more spokes or partial spokes on a disk, the bound component may be in all or a part of a single or plurality of channels, a single bound component may be in a segment of the disk or a plurality of segments. A disk may be divided up into channels, which may be concentric, radial, eccentric, etc., segments, or other geometric form. One may use pre-fashioned arrays which can then be attached to the solid substrate for processing and reading. The arrays may be circular segments, rectangles, circles or other geometric form.

In addition, by using headers one can code for an address. Thus, by using pits or bars having different sizes and/or different spacing, one can create coding which will define the track, segment or other feature associated with one or more bound components. By knowing what was introduced onto the solid substrate in conjunction with the header, one can read what is present at a particular site on the solid substrate. The headers can be placed in conjunction with the various structural elements of the solid substrate or preprepared arrays, so that one can readily determine what the bound component or the labile component is, which is in juxtaposition to the header. The coding can be introduced in any of the conventional ways, such as photolithography and etching, laser burning, chemical erosion, printing or stamping, etc. Alternatively, one may use dots or stripes of fluorescent dyes, the same or different dyes, so as to create an address where one can define the site by the order of emission wavelengths, intensity, size, or the like. In some instances the coding may not be specific for a single entity, it being sufficient to know the identity of a relatively small group, usually under 500 entities, more usually under about 100 entities. By repetitive iteration, one may then determine the specific entity.

Once the solid substrate has been prepared, it may then be used for assaying. Depending on the nature of the bound component and the mobile component, numerous protocols may be employed. The solid substrate will usually be contacted with a fluid form of the mobile component, usually a liquid or solution. As indicated previously, the solid substrate may be completely exposed to a single fluid or different portions of the solid substrate exposed to different fluids. This will depend on the nature of the mobile component and the information to be determined. For example, one may have a cell lysate and one wishes to determine the presence of proteins which can bind to various promoters, homeodomains, other proteins, e.g. transcription factors, membrane protein receptors, carbohydrates and the like. The lysate, subject to prior preparation, could then be added directly to the solid substrate surface. Alternatively, one could have a restriction enzyme genomic digest to determine the presence of one or more sequences. In this case, one would denature the genomic digest to provide single stranded DNA, modify the solution to allow for hybridization, and apply the solution to the solid substrate surface. In some instances one would have modified the DNA to provide tags and/or labels for subsequent processing and/or detection. One would react the sample with a fluorescent compound. Another assay of interest would involve employing a lysate to determine the RNA present in the lysate, where the RNases would first be inhibited, the lysate denature to destroy secondary structure of the RNA and the solution modified to allow for hybridization of the RNA with the nucleic acid bound component.

After the mobile component solution has been added to the solid substrate surface, there will usually be an incubation period for sufficient time for a detectable amount of binding to have occurred, usually at least about 0.5 min and not more than about 12h, usually not more than about 3h and preferably less than about 1h. After the incubation period, the solid substrate surface may be washed to remove non-specifically bound entities, to enhance the stringency of hybridization, to wash away interfering materials, and the like. One or more washings may be employed with varying degrees of vigor, depending on the nature of the components, the degree of affinity between the bound and mobile component and the manner in which the bound component is bound to the solid substrate surface. In some instances reagents may be added to modify the components or the complex between the components. For example, one may add redox reagents to inhibit disulfide formation or enhance disulfide formation, oxidize phenolic compounds, remove redox labile species, etc. After the washing(s), the solid substrate surface may be processed further to provide for identification. In many instances, the mobile component will be tagged, which allows for binding of a highly substituted complementary compound, where the substituents are capable of detection. Ligands and receptors have already been mentioned, but as appropriate, double stranded DNA binding proteins, e.g. RecA, single strand binding proteins, antibodies which bind to the complex but not to the individual components, or the like, may find use. Once the solid substrate surface has been developed so that complexes can be detected, the assay may then be performed with an appropriate reader.

The reader is used with a solid substrate which is divided into coded addressable sites, e.g., sections, channels, segments, etc., with materials of interest, usually biological, at the sites. In effect, those sites where the mobile component has bound to the bound component, in effect forming a complex, would provide a detectable signal. These detectable signals would be associated with a header, identifying the site of the complex. The solid substrate is normally divided into segments and usually linear and/or circular tracks. The preferred embodiment, a disk capable of rotation for addressing different potions of the array, will usually be divided into sectors and circular tracks. A sector, segment and/or track will be associated with a header that provides an address for the sector and/or track. As already indicated, the header may take a variety of forms, such as pits, where the pits may have variable lengths, lines or bars, where the lines or bars may have different thicknesses and spacings, fluorescent dots or lines, or the like. The header will normally be photodetectable and provide for a differentiable signal. The header may be formed using material which has a different reflectivity from the surface of the solid substrate. Where the header consists of pits, the depth of the pits will provide for maximum interference contrast. Different combinations of short and long pits, lines and bars, fluorescers, etc., will indicate the track and sector of the disk. If desired, rather than use a single type of header, different headers may be employed for identifying different sites. The selection of the type of header will relate to the assay being performed to ensure that the header is stable and readable under the conditions of the assay.

The disk scanner or reader will comprise a light source, collimated e.g., laser, or non-collimated, preferably collimated, for optical radiation emission. The wave length of the extinction light will usually be in the UV or visible range ($\sim$250 to 700 nm), but in some situations may be extended into the infra-red, usually below 1000 nm. Conveniently, a beam-shaping module may be used to clean and collimate the beam. A beam splitter can direct the beam into the object lens, which can be mounted on a voice coil, that can move in the x,, y and z directions in relation to the disk surface. The objective lens focuses the excitation light onto the substrate. Light at longer wavelengths than the excitation light is emitted from sites that contain fluorescers.

A spinning motor rotates the disk in relation to the scanner to different sites along a given track and a linear motor moves the scanner along a radial direction to scan over the entire disk. One of the advantages of a spinning disk with addressable sites is that the speed can be varied to get a different level of accuracy, so that one can scan very quickly initially to determine sites on the disk which may then be scanned more slowly. High speed scanning may give rise to relatively low accuracy as a preliminary scan. After the preliminary scan is completed, the scanner can go to specific sites identified during the preliminary scan to collect more data at sites of interest. This allows for rapid and very reliable detection. If one wishes, the scanner may be programmed to only scan one or more sections of the disk.

The objective lens may be used to collect both excitation and emitted light, although two different lenses may be used, one for each beam, where the excitation light could be at an acute angle to the surface and the optics for the emitted light normal to the surface. With a single objective lens, a dichroic beam splitter may be used to direct light at the excitation wavelength to a control path and light at the emitted wavelength(s) into the detection path. Desirably, the excitation light is collected by focusing optics to generate position signals, such as a focusing error signal, tracking error signal, header reading signal and the site number signal, where other than a fluorescent signal is employed for the header. The focusing and tracking error signals are processed and used to control the object lens voice coil to minimize error signals. A DC component of the tracking error signal drives a radial position motor to minimize adverse effects caused by the large objective lens offset and to move the scanner to a different track.

Most of the focusing and tracking signal generation methods for the optical data storage field can be applied to the disk scanner. See, for example, U.S. Pat. No. 5,461,599. As illustrative, a quad-cell detector is placed slightly beyond the nominal focus position of the detector lens. At this position, the spot center is adjusted with respect to the detector center so the focusing error signal (FES) is zero when the disk is in focus. As the disk moves outside of focus, the spot on the detector becomes larger, the FES is less than zero; as the disk moves inside of focus, the spot on the detector becomes smaller and the FES becomes larger. The signal indicates the focus position.

A servo system performance can be improved by using differential focus error detection to eliminate pattern noise. In a differential system, a beam splitter system is used to direct the reflected beam into two paths. One FES is generated in each path. The differential signal is derived from subtracting the two individual FES signals.

The tracking error signal (TES) is derived from the interaction between the optical beam and the structure on the disk. The phase of the diffracted orders is a function of the beam position with respect to the tracking grooves. The diffracted orders interfere with the $0^{th}$ order reflected beam to produce bright and dark modulation at the detector. The TES is derived from subtracting voltage signals of the split sides of the detector. When the beam is centered on track, the $1^{st}$ and $-1^{st}$ orders have the same phase, which creates identical interference patterns. The resulting TES equals zero. When the beam is off the center, the orders have a different phase, which results in one side being stronger than the other, thus a non-zero TES. When the bound component is linked to beads, the actual tracking groove is a series of beads. As the disk spins at a speed faster than the bandwidth of the detection electronics, the averaged tracking error signal reflects the deviation from the center of the track.

As the scanner passes a site, scattering from the edge of the pits of the header, or the actual site, alters the amount of light collected by the detector. Thus, the sum of all detector cells is used to read the header information and to keep track of the site position. This signal is much faster than the focus variation signal, this its effect in focus is averaged out. For other types of headers, one may use different detection systems, such as a bar code reader or use the fluorescent detection system for detecting fluorescent headers, particularly where the emitted light may be of a different wavelength from the light emitted by the component labels. A detector for the different emitted light may be employed, at which time different filters may be used for detecting the light emitted from the header.

In the detection path, the emitted wavelength passes through a filter that rejects the excitation wavelength light and passes the emitted wavelength light, a second blocking filter that selectively blocks the excitation wavelength can also be used to minimize noise from the excitation wavelength. A focusing lens focuses the emitted light onto a detector to measure the fluorescent intensity at that particular site. An alternative embodiment may employ a confocal pinhole and another collection lens can be used to reduce noise.

The disk scanner is also capable of detecting certain arrangements of small arrays, such as square or round microarrays, placed on the disk. Though a spinning square array does not generate a circularly symmetric trace, the tracking voice coil can follow the array by correcting the deviation from rotational symmetry, so long as a track exists on the array. Alternatively, for a small array pattern, such as the square array, an imaging device or small field of view raster scanner may be used in place of the scanner described above to detect each sub-array. Of course, an x-y raster scanner can be used with any array, where either the array moves in relation to the detector or the detector moves in relation to the array. Where an ink-jet printer or other device is used to prepare the array, by placing the bound or sample component at predetermined sites, the same device which is used for preparing the array, may be used in moving the detector to the different sites. The use of the raster scanner allows for rapid positioning of the array with high repeatability, while still allowing the array to comprise a large number of available sites. In one embodiment, the light source is focused onto a line pattern and the line is scanned across the sub-arrays.

Another embodiment is to inject a rapid oscillating signal into the slow tracking error signal to drive the tracking voice coil. The embodiment can be combined with a confocal pinhole to allow ejection of background scattering, and the confocal optics described above. In this embodiment, square arrays can also be placed onto a disk. The scanning may then be performed with the optics previously described for the spinning disk or the raster scanner.

For the electronics and computer control, a detector, such as a photomultiplier tube, avalanche detector, Si diode, or other detector having a high quantum efficiency and low noise, converts the optical radiation into an electronic signal. An op-amp first amplifies the detected signal and then an analog-to-digital converter digitizes the signal into binary numbers, which is then collected by a computer.

Employing conventional servooptics and electronics, the focusing and tracking error signal may be calculated. The signal is dynamically fed into the voice coil to adjust the focus and lateral position of the focused beam to keep the beam on the desired position with the desired size. A special track jump task is performed when the scanner needs to scan other tracks. The same electronics can also read the header information, which is collected by the computer to match position and data signals. A subtraction circuit can be employed to reduce any effect caused by the site geometry, by subtracting the readout signal and the site location signal.

The main body of the software control is a mission control software that controls each of the following subsystems: the motor, subsystem status, synchronization of the data channels, background subtraction, signal enhancement, management of the detected signal with respect to site location to determine a labeled site, graphic user interface, arrangement of the results to display the results in an orderly form for users; and sorting capability on the output.

For further understanding of the invention, the drawings will now be considered. FIGS. 1A and 1B show two different embodiments of conjugated magnetic particles. In FIG. 1A is exemplified a magnetic bead 10 having a coat 12 of streptavidin. A bound component comprising biotin 14, a sequence tag 16, and a nucleic acid 18, is linked to the magnetic bead by the specific affinity of biotin for streptavidin. While only one bound component is shown, it is understood that the magnetic bead would be substantially completely covered with the bound component, there being binding of the bound component, wherever streptavidin is present on the surface. In FIG. 1B an analogous conjugated magnetic particle is depicted with a magnetic particle 10 coated with a covalently bonded receptor protein 20, which could be an antibody to an unnatural oligopeptide sequence 22, defining an epitope to which the receptor protein 20 has a high specific affinity. The oligopeptide 22 is fused to a protein 24 of interest.

Figure 2B:
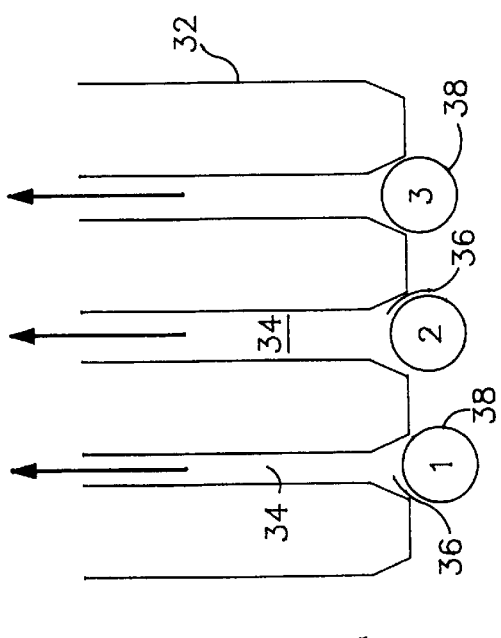
FIG. 2B is a diagrammatic view of particles being bound to a solid substrate by means of vacuum channels.
Figure 2D:
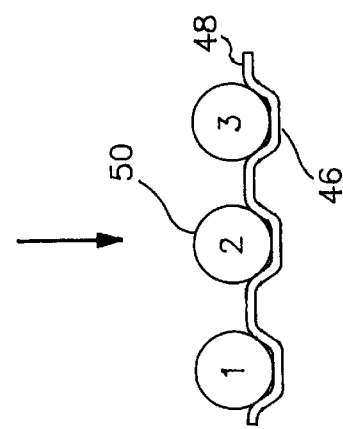
FIGS. 2C and 2D are diagrammatic views of particles sitting in different indentation sites.
Figure 2A:
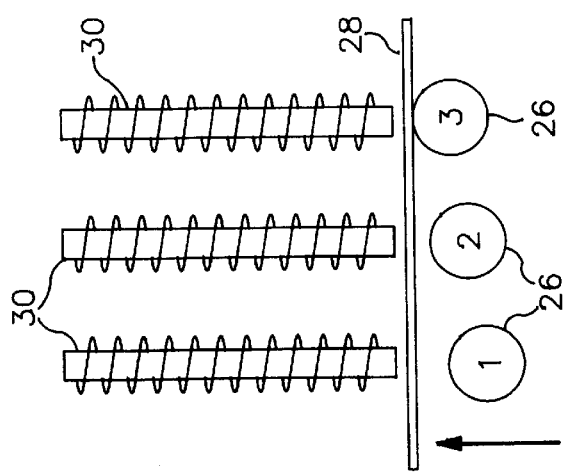
FIG. 2A is a diagrammatic view of particles being bound to a solid substrate by means of magnetized needles.
Figure 2C:
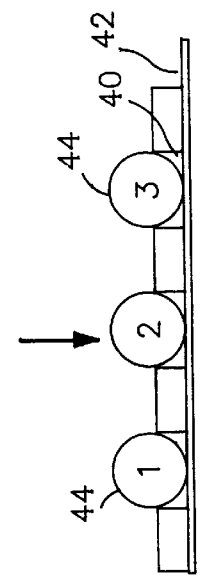

In FIGS. 2A, 2B, 2C, 2D and 2E are depicted variations in ways in which the particles may be arrayed on the surface of a solid support and variations in the shape of the particles to complement the shape of cavities in the surface of the solid support. In FIG. 2A are depicted magnetic particles 26 to which are bound bound components, not shown. A solid substrate 28 has indents for receiving the magnetic particles 26. To orient and hold the magnetic particles 26 are electromagnetic pins 30, which can be independently magnetized so as to direct one or more magnetic particles to a particular site on substrate 28. If desired, the substrate 28 may be magnetizable, so that after the array has been formed, the substrate 28 may be magnetized to hold the magnetic particles 26 in their original orientation. In FIG. 2B an alternative method for preparing the array is depicted. A portion of a porous solid substrate 32 is shown having channels 34, which channels 34 have beveled openings 36 into which particles 38 may conveniently rest. The porous solid substrate 32 is loaded with particles 38, by drawing a vacuum in one or more channels 34. By being able to differentially provide a vacuum in an individual channel, one can direct a particle to that channel. The beveled openings 36 accommodate a single particle and when all the beveled openings 36 are filled with particles, one can maintain the vacuum to keep the particles in position during the assay. One may use passive systems as depicted in FIGS. 2C and 2D. In FIG. 2C cylindrical pits 40 are embossed in substrate 42. The particles 44 may be specifically or non-specifically placed in the pits, depending upon whether the particles are individually encoded. If the particles are individually encoded (See, for example, U.S. Pat. No. 5,565,324), then if a particle provides a signal, the particle may be individually isolated and decoded. If however, the particles are not individually encoded, then the particles may be specifically introduced into a particular pit or a site or segment, where a header is provided that provides the definition of the particles. As depicted in FIG. 2D, rounded pits or indents 46 may be stamped in substrate 48 to house particles. In each case, the particles 48 may be magnetic or non-magnetic, and the substrate may or may not be magnetizable. For greater stability the pits in the substrate and the particles as depicted in FIG. 2E may have a variety of shapes, such as a particle with a pyramidal shape 52, cubic shape 54, or conical shape 56. In this way, once the particle has become accommodated in the indent or pit in the substrate, it will be held firmly in position. Of course, the various shapes may be used with other modes for orienting the particles, such as the vacuum orientation. In addition, different shapes may be employed to orient particles to different sites, so that shapes and sizes may be used to provide sections or segments of different particles with different bound components.

Figure 3B:
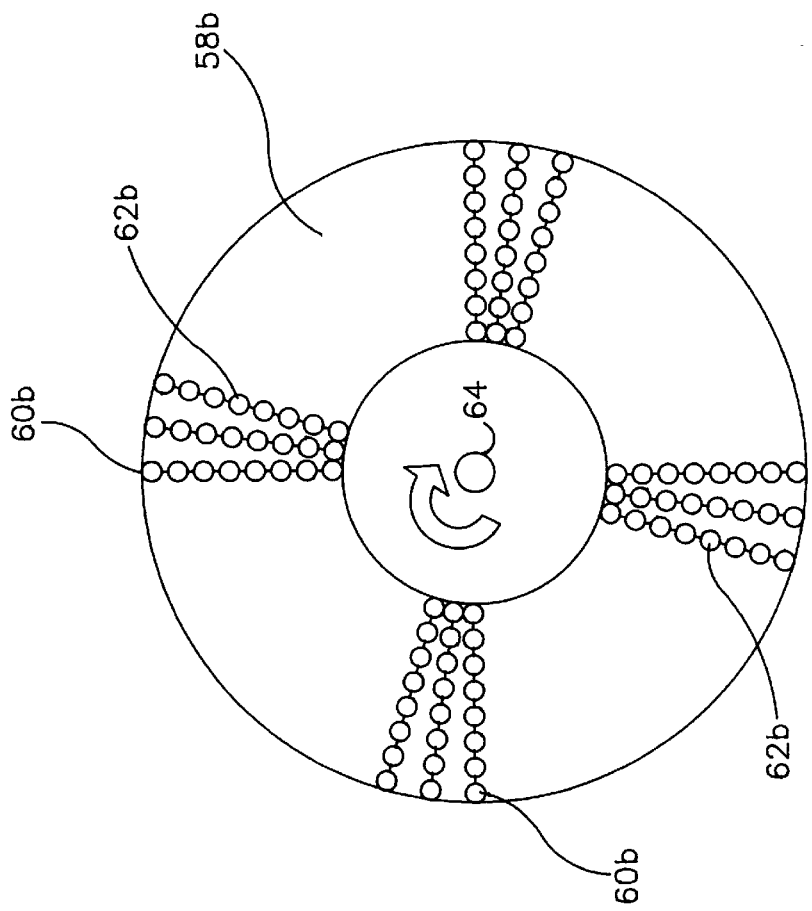
FIGS. 3A and 3B are plan views of solid substrates with different arrays of particles.
Figure 3A:
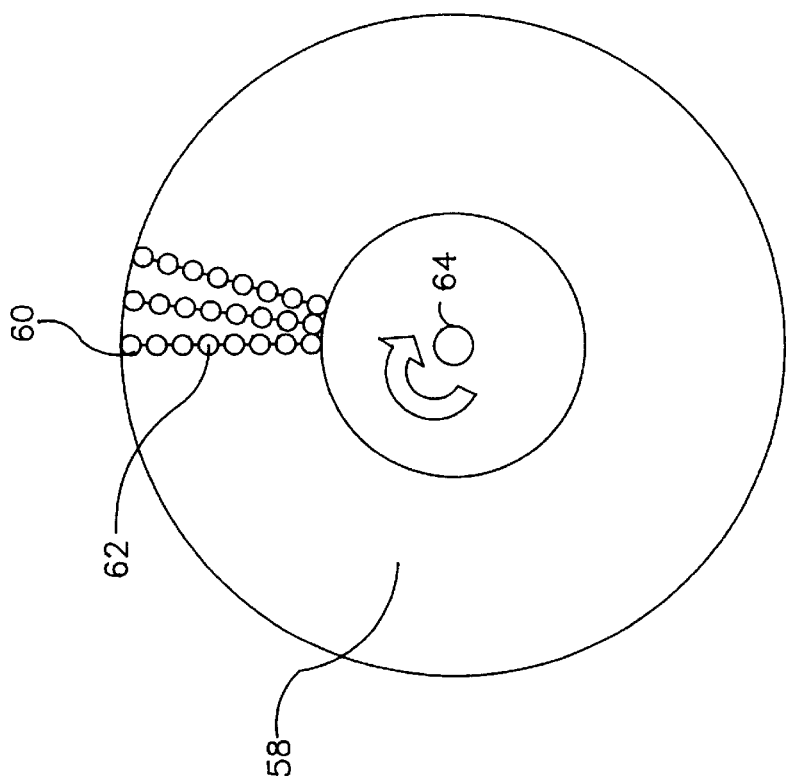
Figure 4:
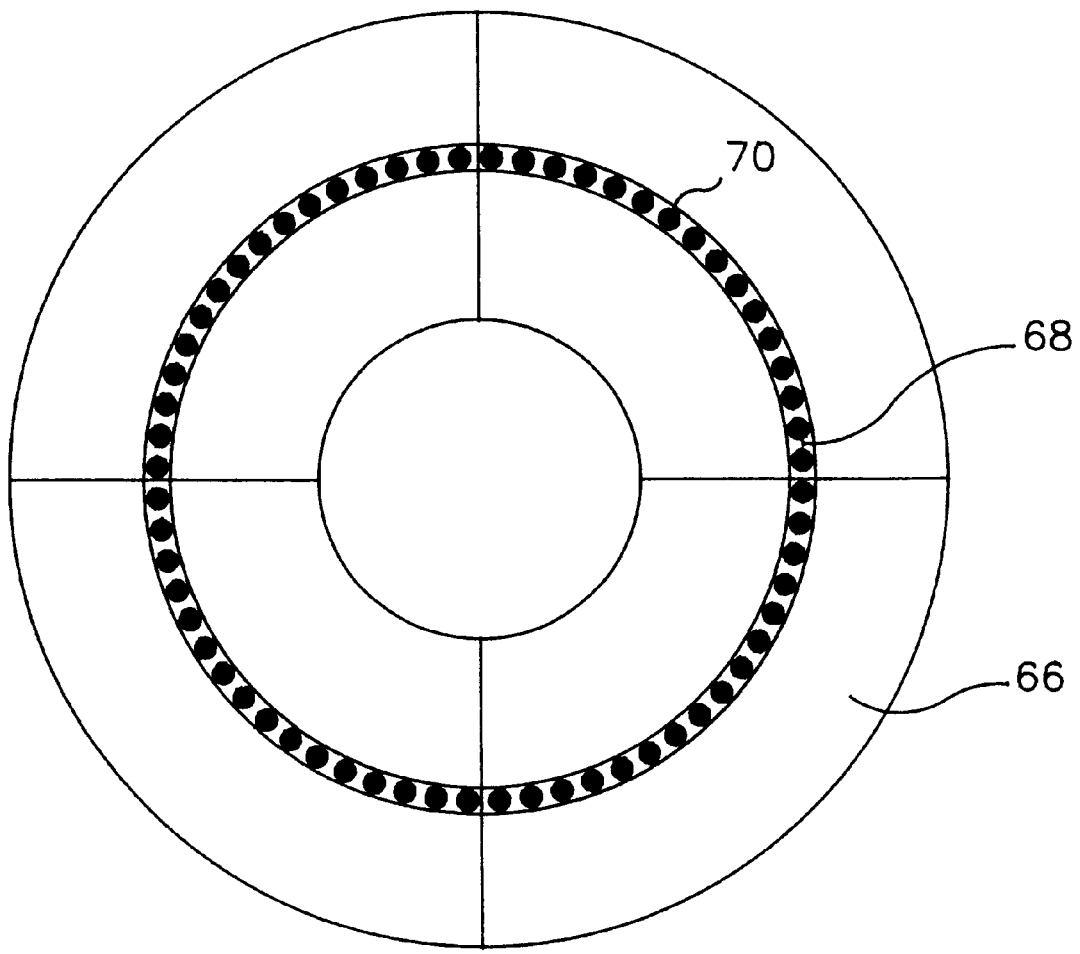
FIG. 4 is a plan view of a solid substrate having a different array of particles according to this invention.

In FIGS. 3A and 3B, two different disks are shown during preparation of the arrays having different radial patterns for the arrays. In FIG. 3A, disk 58 has linear radial arrays 60 of particles, where each spoke 62 may be the same particles or different particles, where each spoke may have a header to define the nature of the particles in the specific spoke and each spoke 62 is added individually. FIG. 3B is analogous to 3A, except that on disk 58b, particles 60b are added in a pattern, so that a plurality of spokes 62b are formed contemporaneously, where the particles 60b in any one position in the pattern of spokes 62b are the same composition, so as to result in sectors having the same organization of compositions. Each of the disks has a central orifice 64 for mounting on a spindle for circular movement. Instead of radial placement of particles and headers, in FIG. 4, disk 66 has a plurality of circular grooves, exemplified by a single groove 68, in which particles 70 are evenly circularly placed. Each groove may have particles having the same or different composition, where for each different composition a different header may be employed in the groove or a different particle, which provides for coding to identify the associated particles.

Figure 5:
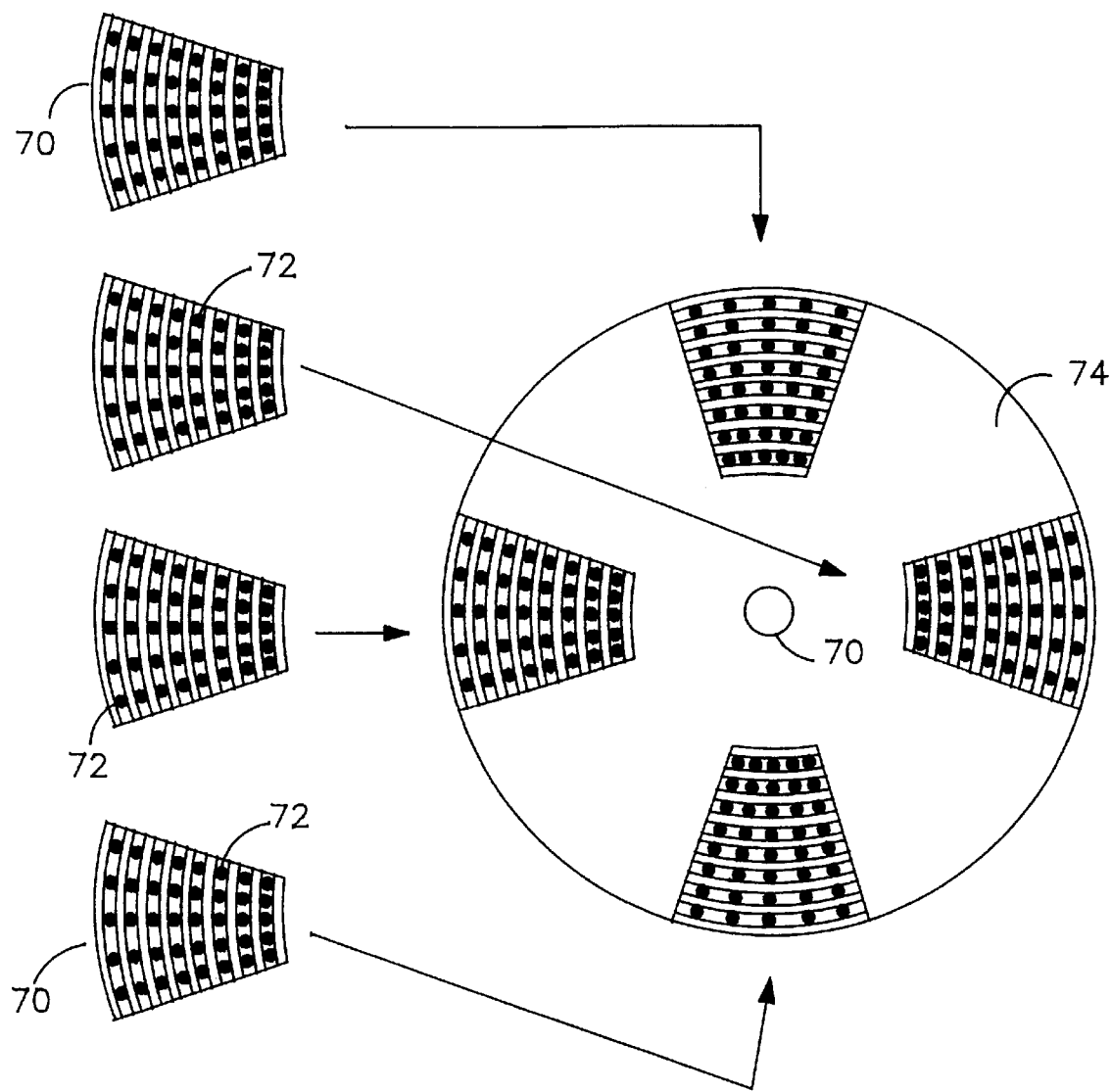
FIG. 5 is a plan view of particle containing segments and their positioning on a solid substrate.

In FIG. 5, the embodiment employs prepared arrays as individual segments. The prepared arrays may take any shape, such as a rectangular, square, parallelopiped, triangular section, or the like. In the figure, segment 70 has a plurality of pits 72 into which particles may be introduced in a predetermined array. The segments 70 may then be positioned on disk 74, being affixed by any convenient means. In FIG. 5 the segments 70 are shown as being radially positioned and separated, as well as spaced apart from the central orifice 76 of the disk 74. It will be understood that the segments may be placed symmetrically or asymmetrically on the disk, preferably symmetrically. The segments may have different numbers of rows 78 and may have the same or different numbers of pits 72 per row 78. Each pit 72, row 78 or segment 70 may have the same or different bound component. The segments 70 may be conveniently processed individually or together to provide the bound component for the assay or for performing the assay. The assay may be carried out with each segment individually and the disk used solely for reading the segments 72 or, if desired, the segments 72 may be arrayed on the disk 78 and the assay carried out on the disk 78. By employing less than an entire disk, one is provided with greater flexibility in assaying samples, while still providing the rapidity and accuracy of the subject invention.

Figure 6:
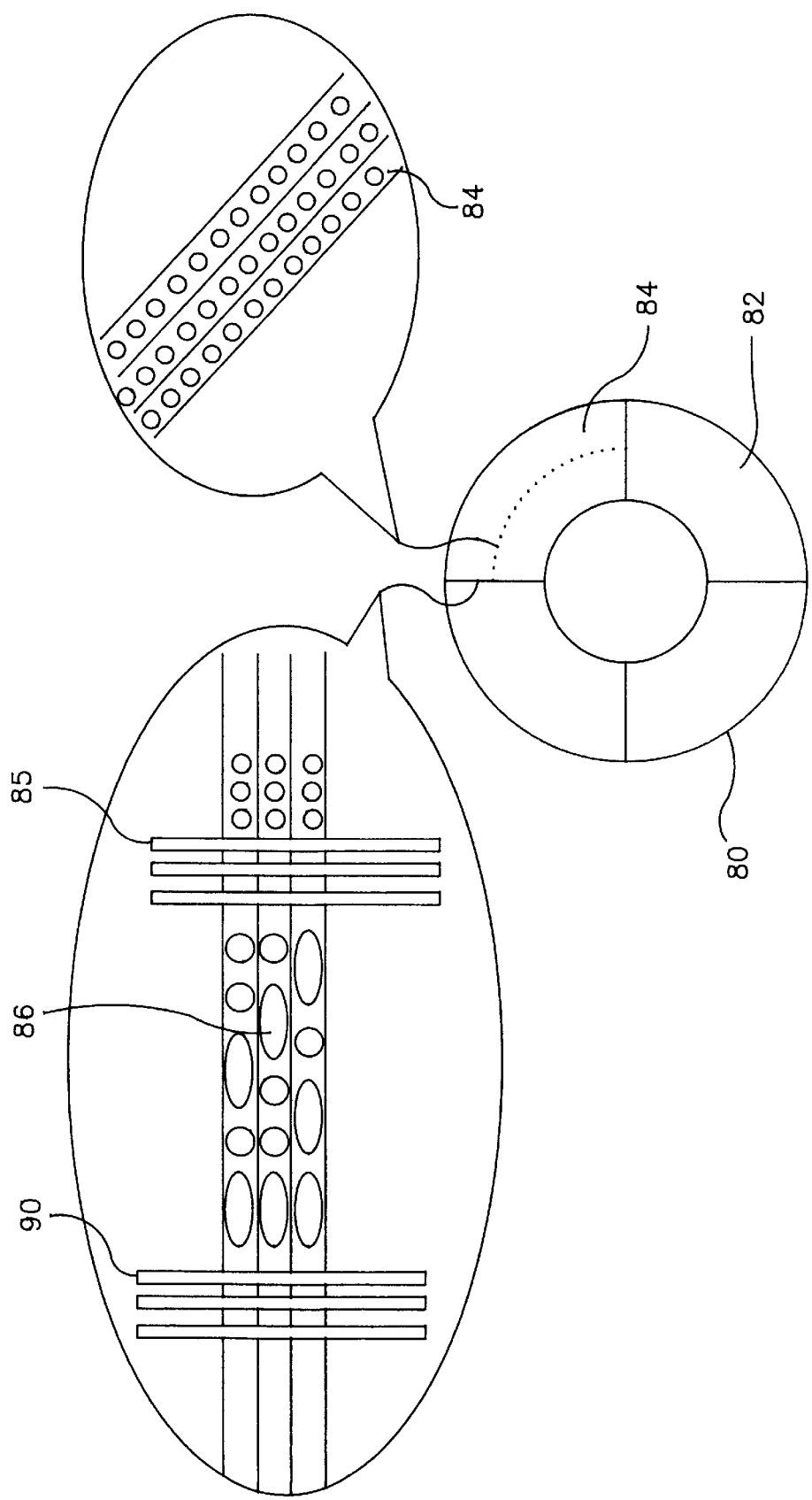
FIG. 6 is a plan view of a solid substrate with exploded portions of the solid substrate.

In FIG. 6 a rotatable disk 80 is divided into separate coded addressable sections. The disk is divided into sectors 82 and circular tracks 84. The beginning of a sector 82 of a given track 84 is a header 86 that describes the information about the sector number and the track number. The header 86 has demarcation lines 88, which segregate the header 86 from the bound component 90 in the tracks 84. The header 86 comprises cavities 90, which are of variable length and may be embossed onto the substrate. The depth of the pits is such that maximum interference contrast is obtained. This can be achieved with depths in the range of about 0.1 to 20µ, more usually 0.25 to 10µ. Different combinations of short and long pits define the information for the sector and track, so as to define the bound component present in the track 84 adjacent the header 86. The site order number within a given track 84 and sector 82 determines the exact location and exact content of the site.

Figure 7B:
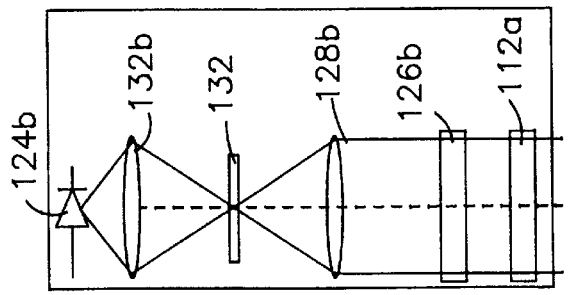
FIG. 7 is a diagrammatic view of an optical system according to the subject invention.
Figure 7A:
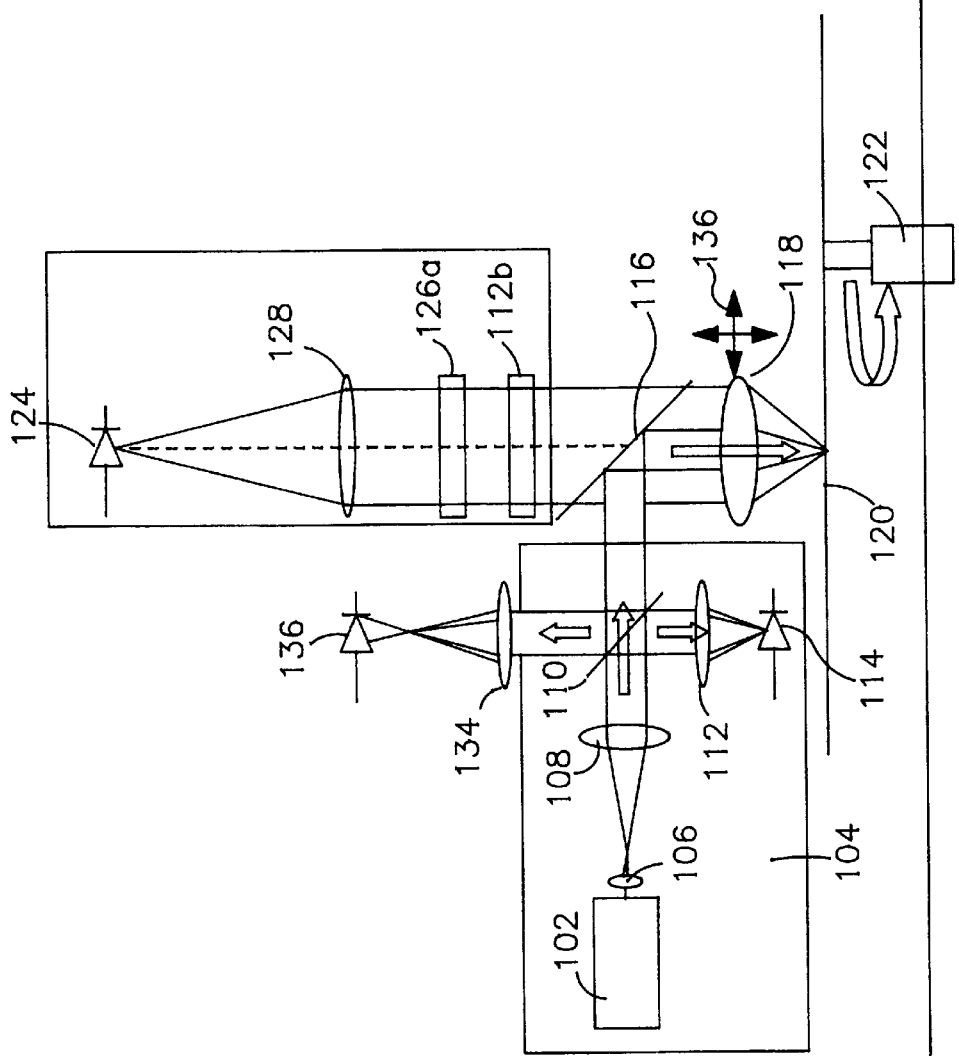

The scanner 100 in FIG. 7A comprises a light source 102 that emits optical radiation and a beam shaping module 104 for shaping the light. The beam shaping module comprises beam shaping optics 106 and 108 to shape the beam which is split by beam splitter 110. The beam splitter 110 directs the excitation light in one pathway to a power monitor comprising a focusing lens 112 and light detector 114 and in a second pathway transmits excitation light to a beam splitter 116, which reflects the excitation light and transmits the emitted light. The beam splitter 110 may be clear glass which allows most of the excitation light to pass through, reflecting only sufficient light to allow light detector 114 to measure the power of the beam. Alternately, the power of the beam may be determined and monitored at the light source. Excitation light from beam splitter 116 is returned to beam splitter 110, where it is reflected into a third pathway for monitoring focus and tracking. Objective lens 118 focuses the excitation light from beam splitter 116 onto the disk 120. The disk is rotated by motor 122 at a predetermined speed, which may be varied depending on the signal received by the emitted light detector 124. Excitation light in the third pathway is directed through focusing optic 134 to focus, tracking and header surface detector 136. Position signals are generated, such as focusing error signal, tracking error signal, header reading signal and site number signal. The focusing and tracking error signals are injected into the objective lens voice coil 136, which holds the objective lens 118 and moves the objective lens 118 in relation to the disk 120 to minimize error signals. A fair degree of latitude is permitted where the variation in focus caused by the bead may be ignored, particularly where the bead diameter is greater than about 10µ and a numerical aperture diameter is selected to accommodate the bead size. More importantly, the focus control will compensate for any wobble in the disk. A DC component of the tracking error signal drives a radial position motor (not shown) to minimize adverse effects caused by large objective lens offset and to move the scanner to a different track. The emitted light detection module comprises objective lens 118, beam splitter 116, filters 112 and 126, a focusing lens 128 and detector 124, which may be a silicon diode, photomultiplier tube, avalanche photodetector, etc. An alternative light detection module 130 is depicted in FIG. 7B, comprising filters 112a and 126b, lower focusing lens 128b, pinhole 132, collection lens 132b and detector 124b. With this arrangement, confocal detection is employed.

In the detection path, the emitted wavelength passes through a filter 126a or 126b that rejects the excitation wavelength and passes emitted wavelength. A second blocking filter 112b or 112a, respectively, that selectively blocks the excitation wavelength may also be used to further minimize noise from the excitation wavelength.

The disk scanner is also capable of detecting certain arrangements of small square microarrays fixed onto the disk. Though a spinning square array does not generate a circularly symmetric trace, the tracking voice coil can follow the array by correcting the deviation from rotational symmetry, as long as a track exists on the array. Alternatively, for the square gene array pattern, an imaging device or small field of view raster scanner can be used in place of the gene scanner to detect each square sub-array.

The address allows rapid positioning of the array wit high repeatability, while still allowing the array to hold a large number of available sites. One particular embodiment focuses the light source onto a line pattern and scans the line across subarrays.

Figure 8:
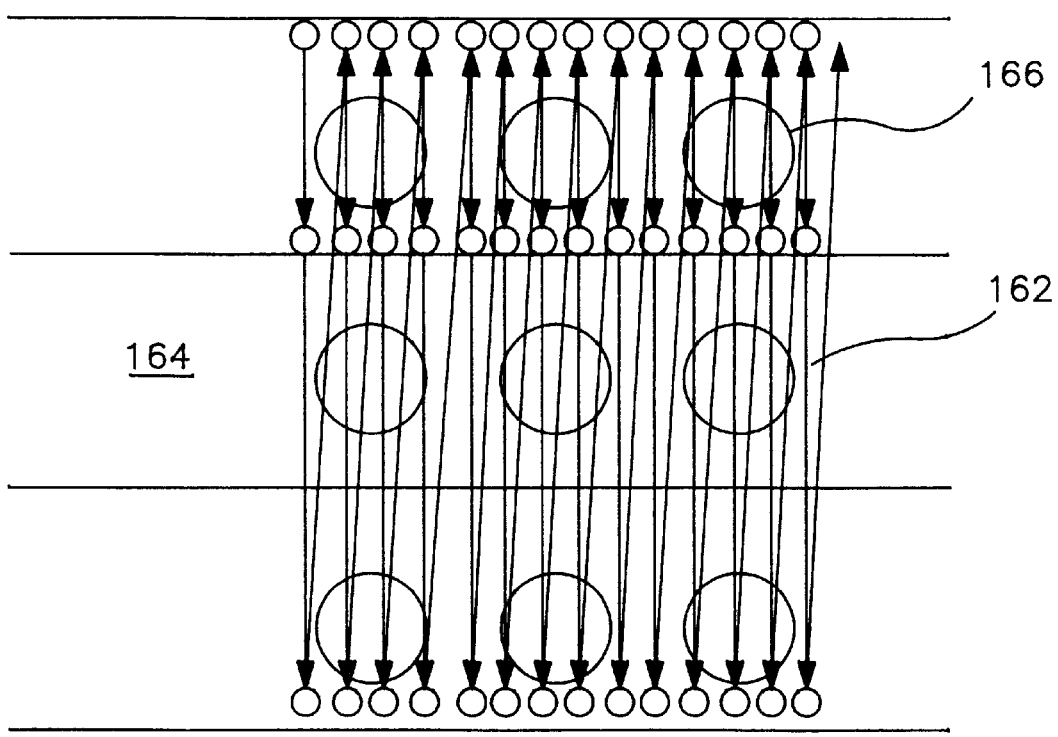
FIG. 8 is a pictorial depiction of the use of raster scanning of a solid substrate.

Another embodiment of the invention depicted in FIG. 8 is to inject a rapid oscillating signal into the slow tracking error signal to drive the tracking voice coil to raster scan the track as depicted by lines 162. The beam moves across beads in one or more tracks 164, using a small beam, so that confocal detection may be employed and one may read one or more tracks. FIG. 8 shows a plurality of tracks 164 scanning over beads 166, with a focused laser beam (not shown) focused onto a track 164.

Figure 9A:
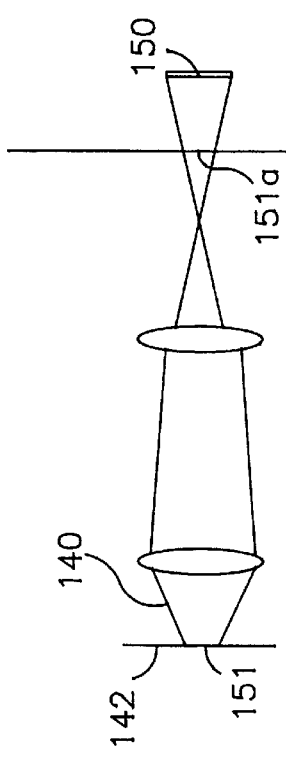
Figure 9B:
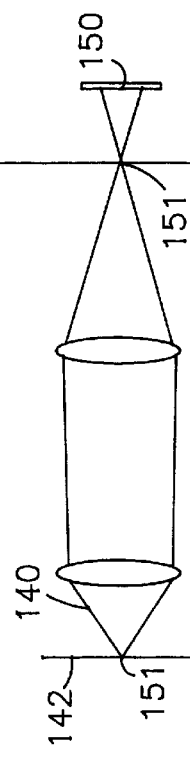
Figure 9C:
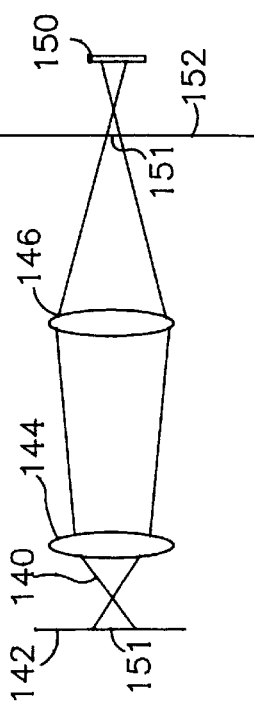

The manner in which tracking is maintained is depicted in FIGS. 9 and 10. FIGS. 9A, 9B and 9C depict three different situations, outside focus, focus and inside focus, respectively. The spot size 151 changes as one moves in and out of focus. In FIG. 9, excitation light rays 140 from the disk 142 pass through the objective lens 144 and servo lens 146, which are depicted in FIG. 7 as lens 134, to quad-cell detector 150. The quad-cell detector 150 is placed slightly beyond the nominal focus position of the servo lens 146. At this position, the spot center 154 is adjusted with respect to the detector center so that the focusing error signal (FES) is zero when the disk is in focus (FIG. 9B). The center 154 of the spot provides that the signal received by quadrants A and B should always be greater by a specific amount and ratio than the signal received by quadrants C and D. Any deviation from these values will indicate that the optical system is out of focus. The nominal focus is depicted along line 152.

The FES is calculated with the formula:

$$FES = \frac{\alpha(A+B)-(C+D)}{A+B+C+D}$$

This signal indicates the focus position, $\alpha$, is an adjustable electronic gain factor. A, B, C and D are determined by the measure of the voltage signal in each of the quadrants of the detector. The servo system performance is improved by using differential focus error detection to eliminate pattern noise. In a differential system, a beam splitter is used to direct the reflected beam into two paths. One FES is generated in each path. The differential signal is derived from Subtracting the two individual FES signals.

The tracking error signal (TES) is derived from the interaction between the optical beam and the structure on the disk. The phase of the diffracted orders is a function of the beam position with respect to the tracking grooves. The diffracted orders interfere with the $0^{th}$ order reflected beam to produce bright and dark modulation at the detector, as shown in the shaded area in FIG. 10B. The TES is derived from subtracting voltage signals of the split sides of the detector. When the beam is centered on track, the $1^{st}$ and $-1^{st}$ orders have the same phase, which creates identical interference patterns. When the beam is off center, the two orders have a different phase, which results in one side being stronger than the other, thus a non-zero TES. When the bound component is linked to beads, the actual tracking groove is a series of beads. As the disk spins at a speed faster than the bandwidth of the detection electronics, the averaged tracking error signal reflects the deviation from the center of the track. As the scanner passes a site, scattering from the edge of the pits of the header or the actual site alters the amount of light collected by the detector. Thus, the sum of all detector cells is used to read the header information and to keep track of the site position. This signal is much faster than the focus variation signal, thus its effect in focus is averaged out.

TES, is calculated by the following formula:

$$TES = \frac{(A+D)-(B+C)}{A+B+C+D}$$

Figure 10A:
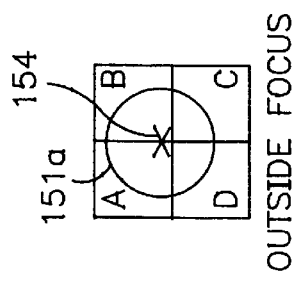
FIGS. 9 and 10 are diagrammatic depictions of the different situations involving changes in focus of the optical system at the solid substrate surface.
Figure 10B:
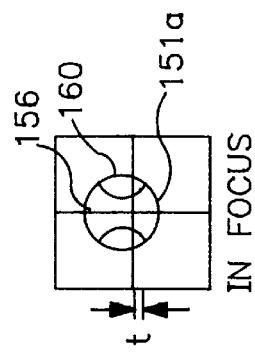
Figure 10C:
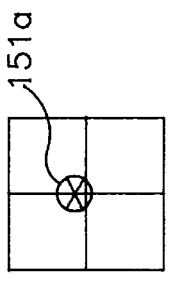

The appearance of the light on the detector is shown in FIGS. 10A, 10B and 10C, which correspond to the situations in FIGS. 9A, 9B and 9C, respectively. In FIG. 10A, the outside focus is depicted, in FIG. 10B in focus 156 is depicted where the shadows 160 are as a result of diffraction from the tracking of the disk. FIG. 10C depicts the view for inside focus.

The electronics and computer control diagram is shown in FIG. 11. A detector 166 converts the optical radiation into an electronic signal. An op-amp 170 amplifies the detected signal from the detector 166, which amplified signal is digitized by analog-to-digital converter 172 to provide digitized numbers. The digitized numbers are collected by the computer 174 and used to determine the presence of a label or other signal generating entity. The results are then forwarded to a display device 176, which may be a monitor, printer, speaker or other device which will indicate the results. The information may be further processed to provide graphs, line or bar, numerical presentation or the like.

Servooptics and electronics 180 as depicted in FIG. 11 calculate the focusing and tracking error signal. This signal is dynamically fed into the voice coil 182 to adjust the focus and lateral position of the focused beam to keep the beam on the desired position with a desired size beam. The beam is monitored by the power monitor detector, which feeds the voltage signal to the computer 174. Any deviation from the predetermined power of the light source is detected and the light source 186 modified to regenerate the desired power. The header and site location detection system 190 feeds the information concerning the focus and site of the beam in the track to the servo signal device 180, which then modifies the voice coil 182 accordingly. The computer monitors the spin motor 192 to regulate the speed of the motor, which may be constant, vary with the signals received from the disk, or be varied in accordance with a predetermined program. The same electronics can also read the header information, which is collected by the computer 174 to match position and data signal. Each site also generates a site location signal from the header electronics, which signal collected by the computer is used to match the exact position and the readout signal. A subtraction circuit can be used to reduce any effect caused by the site geometry, by subtracting the readout signal and the site location signal.

The software for the subject device may comprise a mission control software that controls each of the following systems: the motor, sub-system status, synchronization of various data channels, background subtraction, signal enhancement, management of the detected signal with respect to site location to determine labeled sites, graphic user interface, arrangement of the results for orderly display or reporting and sorting capability on the output.

The subject invention provides for a rapid method to detect interactions between two different components. The method and device allows for screening large numbers of different substances simultaneously or sequentially, providing for direct comparisons of the interactions between different substances. The results can be rapidly read and recorded. The methodology permits the detection of interactions between nucleic acid strands, proteins with proteins and nucleic acid strands, carbohydrate and lipids with each other or other types of compositions in discovering drugs, doing diagnostic assays, forensic medicine, investigating cellular pathways, and the like.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A system for screening a plurality of components comprising a bound group and a mobile group, said mobile group being labeled either directly or indirectly with a light detectable label, said system comprising:

A. a solid substrate comprising a circular disc having a plurality of concentric tracks of a cross-section in the range of 5 to 5000 µm;

particles located at different sites in said tracks, wherein each particle is conjugated with a binding molecule;

headers in said tracks providing distinctive light signals, wherein each header identifies a particular binding molecule;

B. optical means for irradiating said sites to produce a detectable light signal in the presence of label and optical moving means for maintaining said optical means in focus with said solid substrate;

C. a reader for reading said headers and detecting said signal at each of said sites;

D. a focus detector positioned for receiving light from said solid substrate and transmitting a focus signal in relation to the position of said light received by said focus detector; and E. means for connecting to an electronic circuit for transmitting said signals from said reader for determining the presence of a label at said site, said signal indicates the binding of said bound member to said mobile member, and means for receiving said focus signal from said focus detector and directing said optical moving means to move said optical means to maintain said optical means in focus at said sites.

2. The system according to claim 1, wherein said tracks comprises a plurality of indentations for receiving said particles.

3. The system according to claim 1, further comprising:

printing means for depositing said binding members at specific sites on said solid substrate.

4. The system according to claim 3, wherein said printing means comprises an ink-jet printer.

5. The system according to claim 1, further comprising a motor and platform for rotating said disk.

6. A circular disk comprising:

a plurality of concentric tracks of a cross-section in the range of 5 to 5000 µm;

particles in said tracks, wherein each particle is conjugated with a binding molecule;

headers in said tracks providing distinctive light signals, wherein each header identifies a particular binding molecule.

7. The circular disk according to claim 6, wherein said headers comprise indentations, at least two being of different dimensions.

8. The circular disk according to claim 6, wherein each track has a plurality of depressions for receiving said particles.

* * * * *